United States Patent [19]
Dudar et al.

[11] Patent Number: 5,495,855
[45] Date of Patent: Mar. 5, 1996

[54] BLOOD SAMPLING UNIT WITH PROTECTED NEEDLE AND A METHOD FOR SAMPLING BLOOD

[75] Inventors: Thomas E. Dudar, Palatine, Ill.; Peter Graham, Pinckney, Mich.

[73] Assignee: Baxter International Inc., Deerfield, Ill.

[21] Appl. No.: 368,563

[22] Filed: Jan. 4, 1995

[51] Int. Cl.⁶ ................................................. A61M 5/00
[52] U.S. Cl. .......................... 128/763; 604/198; 604/263
[58] Field of Search ............................ 604/198, 110, 604/187, 263, 192; 128/763–765

[56] References Cited

U.S. PATENT DOCUMENTS 5,403,286  4/1995  Lockwood, Jr. ............... 604/198 X

OTHER PUBLICATIONS

Becton Dickinson, Interlink Blood Collection Assembly, 1994, U.S.A.

*Primary Examiner*—John D. Yasko
*Attorney, Agent, or Firm*—Jeffrey C. Nichols; Paul C. Flattery; Mark J. Buonaiuto

[57] ABSTRACT

A protective shield for a blood sampling unit that is movably engaged to an adapter having a needle attached. The shield attaches to a tube holder when the needle is covered by the shield. Longitudinal grooves on the adapter guide the shield between a first position, covering the needle, and a second, position, exposing the needle. The shield can be locked in either the first position or the second position. The blood sampling unit is safely disassembled or reassembled when the needle is covered by the shield. In an embodiment of the invention, a tip protector, removably attached to the adapter, extends through the length of the tube holder to prevent needlesticks. The blood sampling unit and the tube holder can be assembled and disassembled when the tip protector is attached to the adapter, covering the needle. The tip protector is removed during a clinical procedure and then replaced after the clinical procedure is finished.

9 Claims, 5 Drawing Sheets

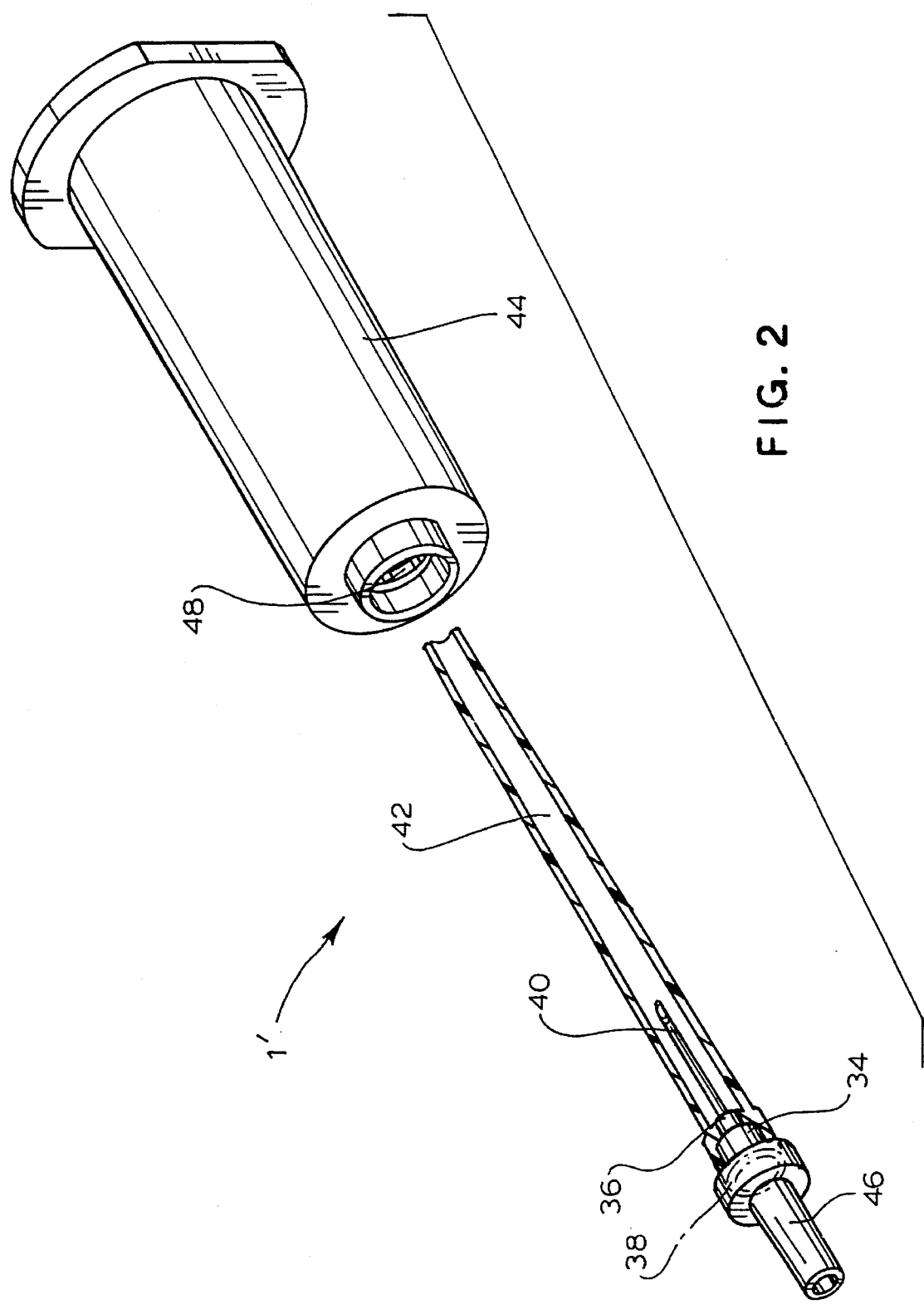

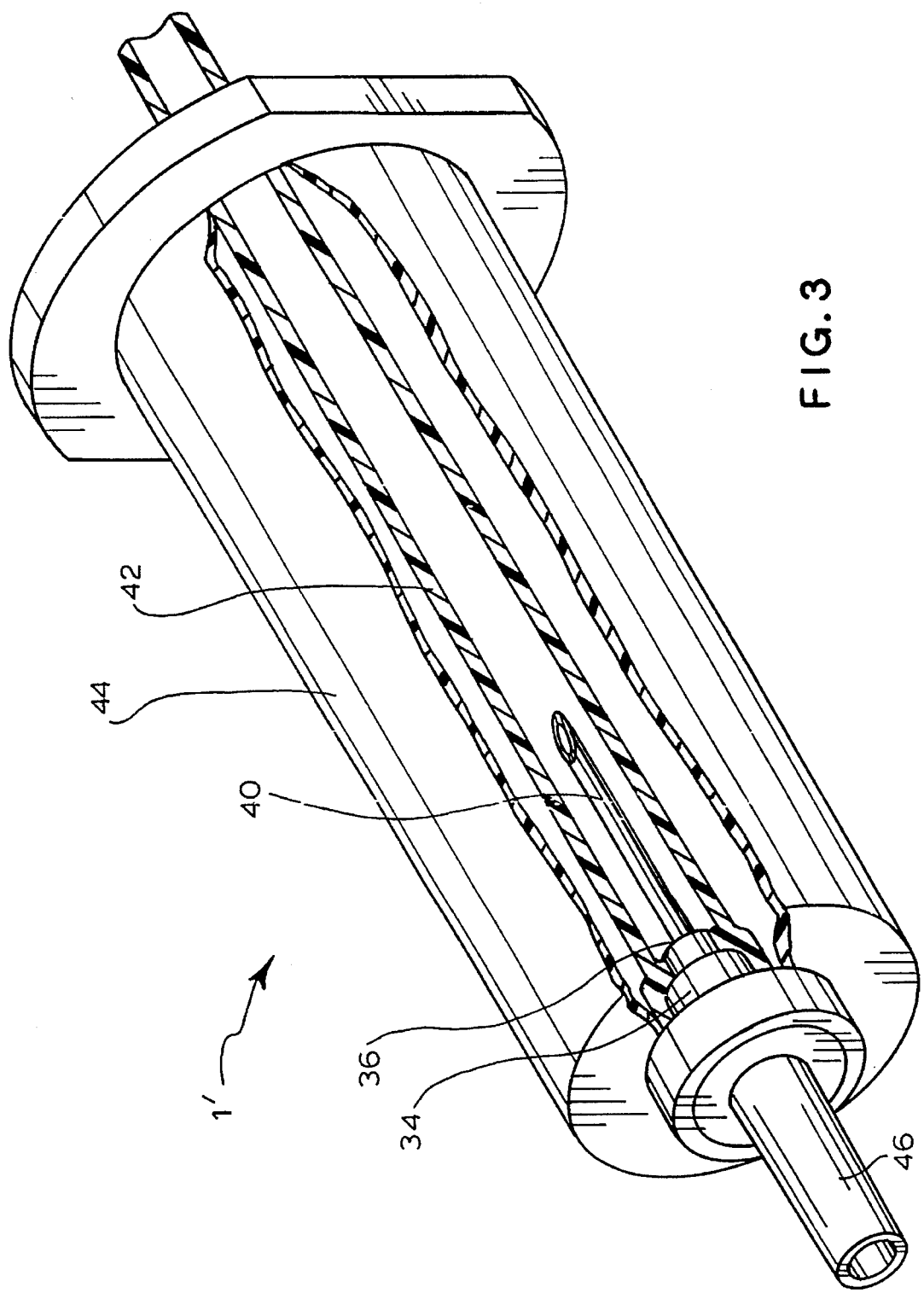

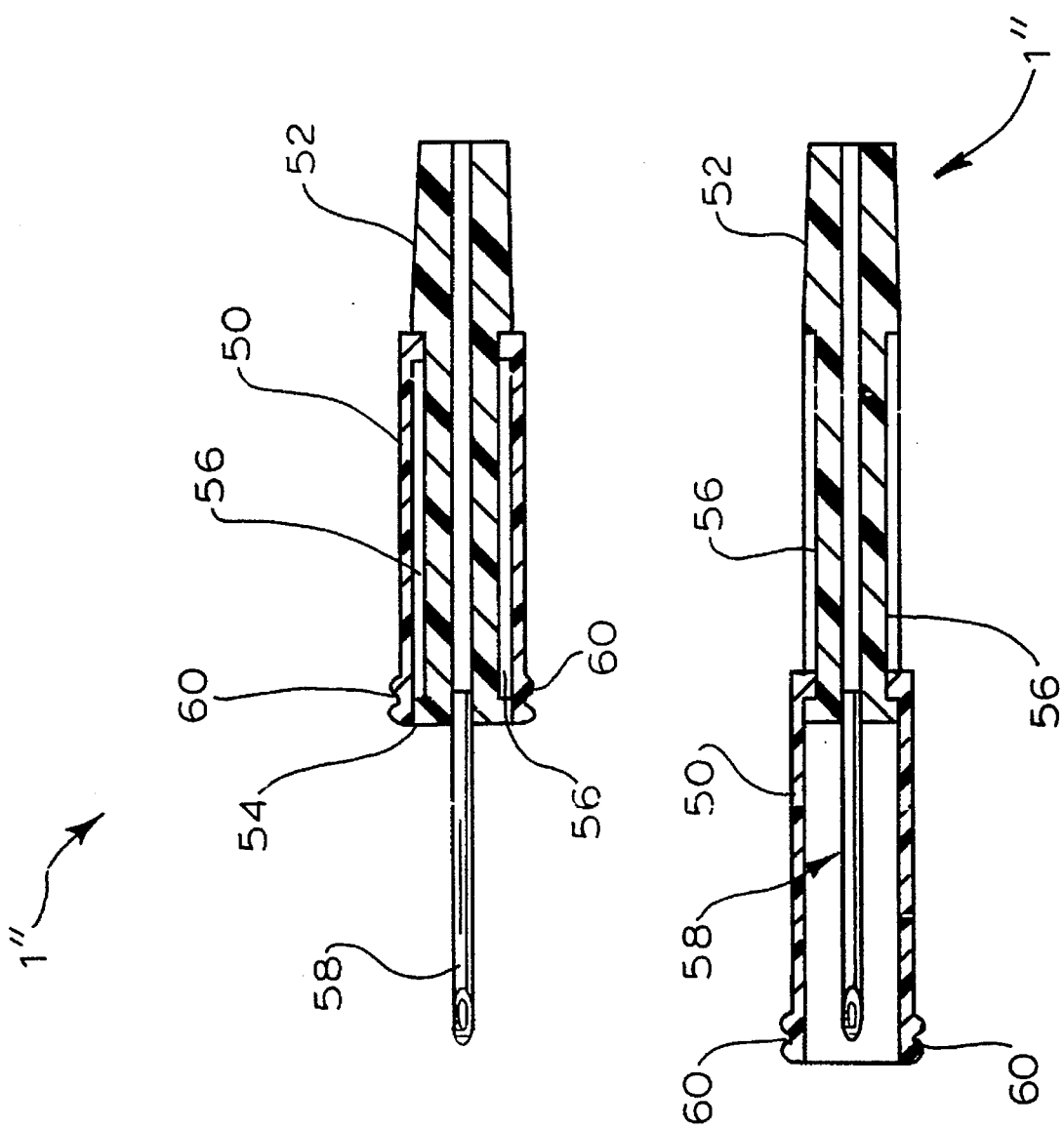

BLOOD SAMPLING UNIT WITH PROTECTED NEEDLE AND A METHOD FOR SAMPLING BLOOD

BACKGROUND OF THE INVENTION

The present invention generally relates to a blood sampling unit and a method for sampling blood used for injection of medication or withdrawal of blood and fluid samples from a patient or donor. More specifically, the invention relates to protecting individuals from unintentional contact with an exposed needle point during assembly, use and disassembly of an evacuated tube blood sampling unit used for clinical procedures.

It is, of course, known to collect blood from an individual and test same. Such testing may be performed for diagnostic procedure or as part of blood collection.

For example, when a unit of blood is collected from an individual, one or more sample tubes of blood are collected. Samples for routine hematology analysis are collected from venous blood. Most commonly, the blood is pulled by a vacuum into sealed evacuated containers. The blood samples are then subjected to various tests, e.g., compatibility.

A conventional device used for blood sampling includes an adapter having, at a first end, a pointed cannula for accessing a tube, such as an evacuated tube. A threaded hub is located in the middle of the adapter allowing the adapter to be received by a holder for holding the evacuated tube. At a second end of the adapter, a second cannula for accessing a blood fluid flow path is provided.

To use the conventional blood sampling device, a tip protector covering the pointed cannula of the first end of the adapter is removed, exposing the pointed cannula. The adapter is then threaded into a tube holder.

Once the adapter is threaded onto the tube holder, the conventional clinical procedure of drawing blood can be performed. To this end, a second cannula, opposite the tube holder accesses the blood flow path. A vacuum tube is placed within the tube holder and receives the pointed cannula located within the tube holder. Blood will thereby flow from the blood flow path into the vacuum tube.

Because pointed cannulas are used, the adapter and method of collecting samples of blood provides the risk of accidental needlesticks. Although protective covers have been designed to reduce the risks of accidental needlesticks, in order to use the device, the covers must be removed.

A still further risk of needlesticks occurs when the adapter must be disposed of. After the clinical procedure is completed, the adapter and the contaminated needle must be disposed. Either the entire unit is disposed of, or the adapter and the needle are detached from the tube holder so that the tube holder can be reused. In any event, the sharp needle is once again exposed during disassembly.

Unfortunately, accidental needlesticks of healthcare personnel are common. Transmission of HIV by accidental needlesticks is estimated at about one out of every two hundred accidents. Risk of transmission increases by deep injections or injection of blood at the time of the needlestick. It is also known that hepatitis B is more frequently and easily transmitted than HIV by accidental needlesticks. While the risk of HIV transmission appears to be much lower than that of hepatitis B transmission, the potential consequences are much worse. See Merck Manual, 16th Edition, p. 79.

In addition to the use of covers, other attempts have been made to solve the problem of potential dangerous contact with both ends of the blood sampling unit. Recently, a blunt cannula, such as the Interlink® blunt cannula, has been used to prevent accidental needlesticks at a second end of the adapter, i.e., the end that accesses the blood fluid flow path. However, the first end of the adapter, because it is designed to pierce a rubber septum of an evacuated test tube, must be pointed. Thus, such adapter still provides the risk of accidental needlesticks.

A need, therefore, exists for an improved blood sampling device and a method for sampling blood to avoid potentially dangerous accidental needlesticks.

SUMMARY OF THE INVENTION

The present invention provides a blood sampling unit with means for preventing accidental needlesticks during assembly, use and disassembly of the blood sampling unit.

To this end, in an embodiment, the present invention provides a blood sampling unit comprising an adapter having a proximal end and a distal end, a shield and a tube holder. The distal end of the adapter includes a pointed cannula. The shield that includes a first end and a second end, is coupled to the adapter at the first end and is selectively movable between a first position and a second position. The shield covers the needle when in the first position and exposes the needle when in the second position. The tube holder is attachable to the shield.

In an embodiment, the blood sampling unit includes a blunt cannula located at the proximal end of the adapter that is designed to access a blood fluid flow.

In an embodiment, the second end of the shield of the blood sampling unit is threaded for allowing attachment to the tube holder.

In an embodiment, the shield of the blood sampling unit is slidably engaged to the adapter.

In an embodiment, the shield of the blood sampling unit is threadably engaged to the adapter.

In an embodiment, the blood sampling unit further comprises means for locking the shield in the first position and the second position.

In another embodiment of the present invention, a blood sampling unit is provided comprising an adapter having a proximal end and a distal end. A pointed cannula is coupled to the distal end of the adapter. The adapter is designed to be coupled to a tube holder. The tube holder has an opening at one end thereof. Removable means are provided for covering the cannula. The removable means are so constructed and arranged so that, when attached to the distal end of the adapter and the adapter is coupled to the tube holder, the removable means extend for a length of the tube holder and a portion thereof extends through the opening.

In an embodiment, the blood sampling unit further comprises a blunt cannula attached to the proximal end of the adapter.

In another embodiment, the present invention provides a method for sampling blood comprising the steps of: providing an adapter having a proximal end and a distal end, each of the ends including a cannula extending therefrom; providing a member that is coupled to the distal end of the adapter and selectively movable between a first position and a second position, the member arranged to cover the first cannula while in the first position and to expose the first cannula when in the second position; and collecting blood using the first cannula and the second cannula.

In another embodiment, a method is provided for sampling blood comprising the steps of: providing an adapter including a blunt cannula and a pointed cannula; covering the pointed cannula with a cover to prevent accidental contact therewith; coupling the adapter to a tube holder; removing the cover; and puncturing a septum of a tube with the pointed cannula.

An advantage of the present invention is to provide an improved blood sampling unit.

Another advantage of the present invention is to provide needle tip protection during periods of assembly, use and disassembly of the blood sampling unit.

A further advantage of the present invention is to provide a shield that can be used as a needle tip protector for the device, reducing additional components and packaging.

Yet another advantage of the present invention is to provide a safer method for sampling blood.

An additional advantage of the present invention is to provide a shielded needle design that can be used in other applications, e.g., accessing other vial stoppers or injection sites.

Another advantage is to provide a shield or needle tip protector to protect a person from a needle or pointed cannula used to access an evacuated tube.

Still further, an advantage of the present invention is to provide an improved method for avoiding exposure to infectious diseases when sampling blood in a clinical setting.

Additional features and advantages of the present invention are described in, and will be apparent from, the detailed description of the presently preferred embodiments and from the drawings.

BRIEF DESCRIPTION OF THE DRAWINGS

FIG. 2 illustrates a perspective view of another embodiment of the present invention including an unattached blood sampling unit having a cannula, an adapter with a needle protected by a tip protector, and a tube holder.

FIG. 3 illustrates a perspective view of the blood sampling unit illustrated in FIG. 2 attached to a tube holder.

FIG. 4A illustrates another embodiment of the blood sampling unit including an adapter with an attached needle and a shield in a position such that the needle is exposed in accordance with another embodiment of the present invention.

FIG. 4B illustrates a cross-sectional view of the blood sampling unit of FIG. 4A including the adapter with the attached needle and the shield in a position such that the needle is unexposed.

DETAILED DESCRIPTION OF THE PRESENTLY PREFERRED EMBODIMENTS

The present invention provides devices that can be used to collect blood. In this regard, blood sampling units that reduce or eliminate accidental needlesticks are provided.

Pursuant to the present invention, the blood sampling unit includes a shield or a needle tip protector that prevents healthcare personnel from coming into contact with an exposed needle during the assembly, use and disassembly of the blood sampling unit.

Figure 1:
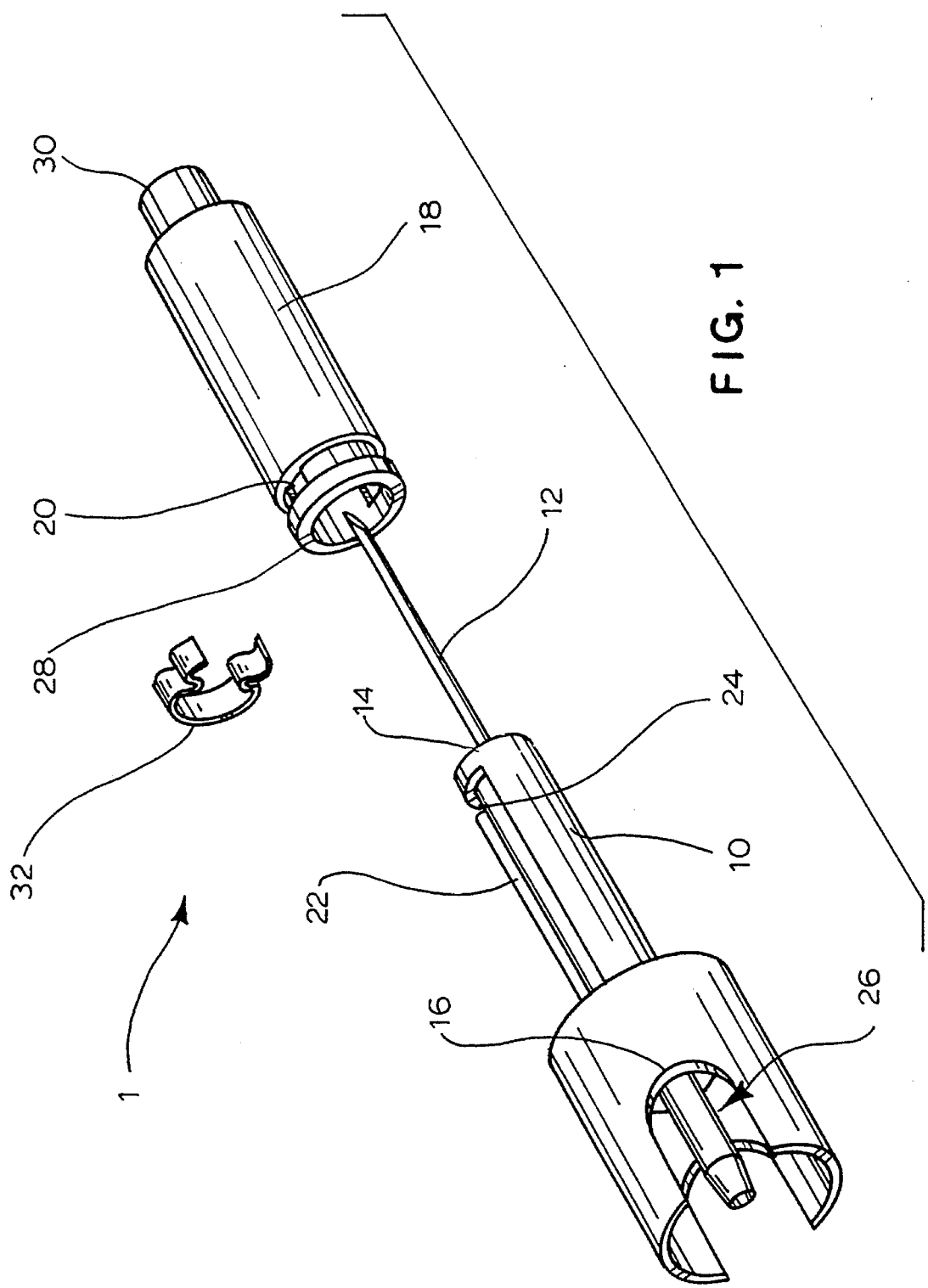
FIG. 1 illustrates a perspective view of a blood sampling unit with a needle protected by a shield in accordance with an embodiment of the present invention.

FIG. 1 of the drawings illustrates an embodiment of a blood sampling unit 1 of the present invention. An adapter 10 is shown having a distal end 14 and a proximal end 16. A needle or pointed cannula 12 is affixed to the distal end 14 of the adapter 10. The needle 12 provides means for accessing an evacuated tube, other types of vial stoppers or injection sites located on a donor.

A shield 18, which is tube-shaped in the illustration, is attachable to the adapter 10. To effect the attachment, a channel 22 is located in the wall of the adapter 10. A first indented portion 20 of the shield 18 is received into the channel 22 allowing the shield 18 to slidably move in the channel 22.

On the proximal end 16 of the adapter 10 is a cannula 26. The cannula 26 preferably is a blunt cannula, such as used in the Interlink® system available from Baxter Healthcare Corporation of Deerfield, Ill. or the Interlink® blunt cannula available from Becton, Dickinson and Company. The cannula 26 provides means for accessing a source of the blood through an injection site on the donor. Using a blunt cannula eliminates potential exposure to needlesticks. The cannula 26 may be replaced by a luer connector (not shown). The luer allows another cannula or a second needle to be attached at the proximal end 16 of the adapter 10.

The shield 18, as illustrated in FIG. 1, has a first end 28 and a second end 30. The shield 18 may be constructed from a variety of materials. For example, the shield 18 can be plastic. The first end 28 of the shield 18 has a larger diameter than the distal end 14 of the adapter 10. Due to the larger diameter, the first end 28 of the shield 18 is capable of sliding over the adapter 10 to assume a first position. The first position protects an individual handling the blood sampling unit 1 from the needle 12 by providing complete coverage of the adapter 10 and the needle 12. The shield 18 can also assume a second position in which the shield 18 exposes the needle 12.

The shield 18 cooperates with the adapter 10 and is selectively positionable along the channel 22. The shield 18 can also be locked in either the first position or the second position. To lock the shield 18 in the first position, the shield 18 is pulled away from the adapter 10 and slightly rotated until a first indented portion 20 on the shield 18 engages a second indented portion 24 on the adapter 10. The user of the blood sampling unit 1 is, therefore, protected from accidental needlesticks.

A guide clip 32, as shown in FIG. 1, can be used to provide compression when locking the shield 18 in the first position or the second position. The guide clip 32 fits into the indented portion 20 located on the shield 18.

The shield 18 also functions to accompany and cover the needle 12 when the blood sampling unit 1 is not in use or in storage, instead of requiring a separate part for this function. Subsequently, the need for additional components and packaging is eliminated, thus improving the economics of producing the blood sampling unit 1.

The second end 30 of the shield 18 is threaded for attachment to a tube holder (not shown). The tube holder can be attached to the shield 18 only when the shield 18 is in the first position. This prevents possible needlesticks from occurring to an individual handling the blood sampling unit 1 during assembly of its parts.

Referring now to FIG. 2, another embodiment of a blood sampling unit 1' is illustrated. An adapter 34 is shown with a needle 40 attached to a distal end 36 of the adapter 34. The needle tip protector 42 may be attached to the adapter 34 by a snapping method or a twisting method. Of course, other methods known to those skilled in the art can be employed. A removable needle tip protector 42 is located at the distal end 36 of the adapter 34. A tube holder 44 is shown unattached to the adapter 34 in FIG. 2.

Referring to FIGS. 2 and 3, the needle tip protector 42 extends for a length of the tube holder 44 such that a portion of the needle tip protector 42 extends through the length of the tube holder 44, when the tip protector 42 is attached to the adapter 34. Therefore, the adapter 34 can be secured to the tube holder 44 with the tip protector 42 in place. Therefore, the needle 40 is fully covered by the needle tip protector 42 eliminating exposure to needlesticks.

The tube holder 44 includes an opening 48 that has a larger diameter than the adapter 34 and the tip protector 42. Therefore, the tube holder 44 fits over the needle tip protector 42 when the blood sampling unit 1' is assembled. This allows the tip protector 42 to be easily removed from the needle 40 after the adapter is attached to the tube holder.

As noted above, after the adapter 34 is attached to the tube holder 44, the needle tip protector 42 is removed. However, after use of the adapter and the tube holder to collect blood, the needle tip protector 42 is placed back on the adapter 34 before the blood sampling unit 1' is disassembled. This thereby prevents accidental needlesticks during disposal of the assembly.

Preferably, a cannula 46 or a connector, such as a luer connector, is attached to the proximal end 38 of the adapter 34. The cannula 46 is preferably a blunt cannula such as that used in the Interlink® system, available from Baxter Healthcare Corporation of Deerfield, Ill. The cannula 46 provides access to the source of the blood, e.g. venous supply of the donor.

Referring now to FIG. 3, the blood sampling unit 1' of FIG. 2 is shown with the tube holder 44 and the adapter 34 in an attached or connected position. The needle 40 and the needle tip protector 42 are attached to the distal end 36 of the adapter 34. As illustrated, the needle tip protector 42 extends through the tube holder 44 so that a portion of the needle tip protector 42 extends through the opening 48 (see FIG. 2) of the tube holder 44. As previously discussed with respect to FIG. 2, the tube holder 44 is safely attached to the adapter 34 when the needle tip protector 42 is attached to the adapter 34, providing full coverage of the needle 40.

FIGS. 4A and 4B illustrate another embodiment of a blood sampling unit 1". In FIG. 4A, a retractable shield 50 is slidably engaged to an adapter 52. The retractable shield 50 includes an end 54. Longitudinal grooves 56 are located in walls of the adapter 52 to provide means for movement of the retractable shield 50 within the grooves 56 of the adapter 52. A needle 58 is attached to the adapter 52. External threads 60 are located on the end 54 of the retractable shield 50 providing a means for attachment of the retractable shield 50 to a tube holder 62 (see FIGS. 5A and 5B).

The retractable shield 50 is designed so as to be locatable in a first position as shown in FIG. 4B. In the first position, the needle 50 is fully covered and unexposed. A second position of the shield 50 with respect to the needle 58 is shown in FIG. 4A. As illustrated, in the second position, the needle 58 is fully exposed. The longitudinal grooves 56 in the adapter 52 allow the retractable shield 50 to transpose selectively between the first position and the second position.

The threads 60 of the shield 50 provide a means for attaching the tube holder 62 (see FIGS. 5A and 5B) to the retractable shield 50. Assembly of the tube holder 62 and the retractable shield 50 is possible when the retractable shield 50 is in the first position, fully protecting the needle 58.

Figure 5A:
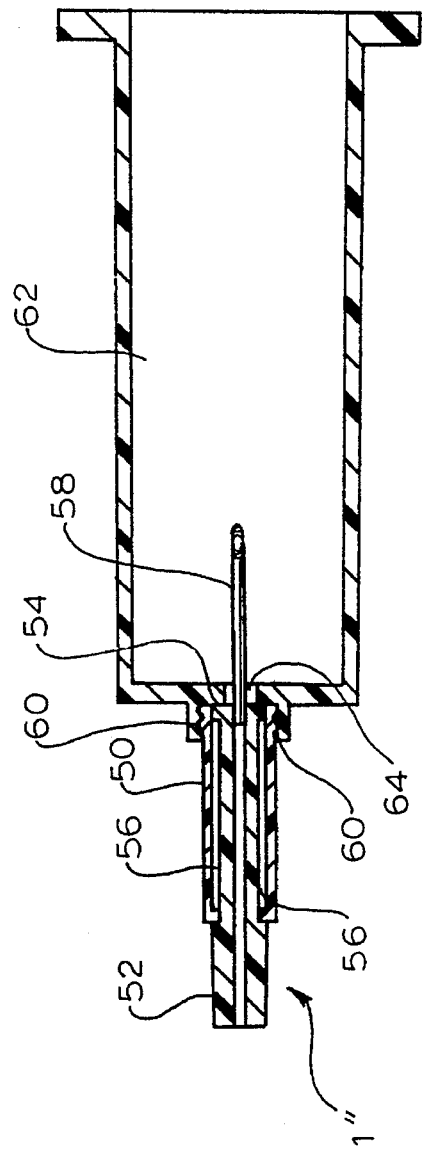
FIG. 5A illustrates a cross-sectional view of a blood sampling unit of FIG. 4A including the adapter with the attached needle and the shield attached to the tube holder.

Referring now to FIG. 5A, the blood sampling unit 1" in FIG. 4A is shown attached to the tube holder 62. The tube holder 62 is shown attached to the end 54 of the retractable shield 50. FIG. 5A illustrates the needle 58 advanced through an opening 64 of the tube holder 62. The needle 58 is advanced after the tube holder 62 has been attached, and the retractable shield 50 is moved into the second position. In this regard, the retractable shield 50 does not interfere with the use of the needle 58 in the clinical procedure.

The needle 58 is advanced to puncture an evacuated tube (not shown). Of course, the needle 58 with the retractable shield 50 can be used to access other types of vial stoppers or injection sites.

Figure 5B:
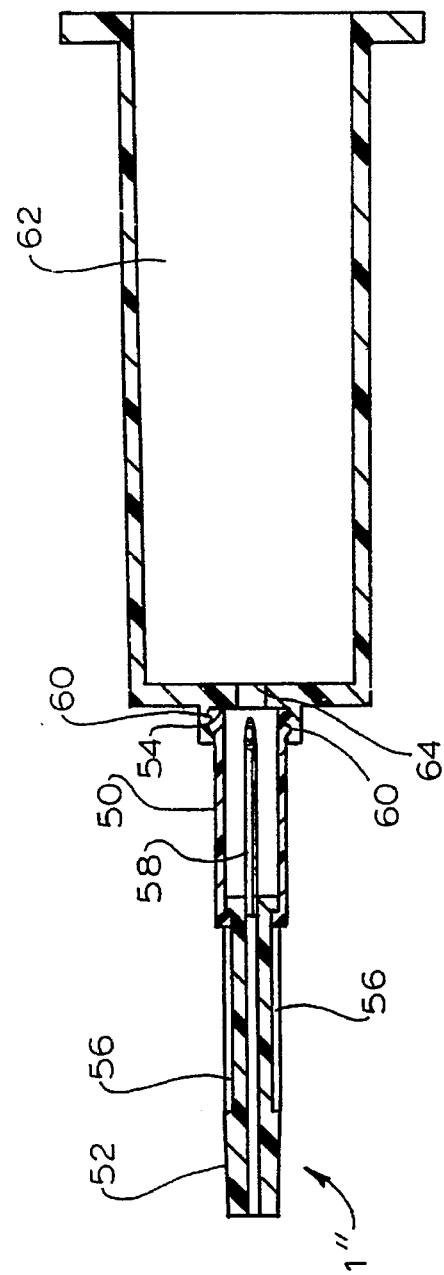
FIG. 5B illustrates a cross-sectional view of a blood sampling unit of FIG. 4B including the adapter with the attached needle and the shield attached to the tube holder.

FIG. 5B illustrates the blood sampling unit 1" in FIG. 4B attached to the tube holder 62. The retractable shield 50 is shown in the first position, fully covering the needle 58. When the retractable shield 50 is in the first position, as illustrated in FIG. 5B, the tube holder 62 can be attached to the end 54 of the retractable shield 50 by the threads 60. Of course, other methods can be used, such as interrupted threads or a cylindrical interface to attach the tube holder 62 to the retractable shield 50.

It should be understood that various changes and modifications to the presently preferred embodiments described herein will be apparent to those skilled in the art. Such changes and modifications can be made without departing from the spirit and scope of the present invention and without diminishing its attendant advantages. It is, therefore, intended that such changes and modifications be covered by the appended claims.

We claim:

1. A blood sampling unit comprising:

a generally tubular tube holder configured to removably retain a blood sampling tube, the tube holder having a rear end defining an opening to allow the insertion and removal of the tube, and a forward end defining an opening;

an adapter extending through the opening of the forward end of the tube holder, the adapter being removably coupled to the tube holder, the adapter having a rear end including a sharp cannula which extends rearward within the tube holder and having a cannula forming a forward end which extends forward from the tube holder; and a shield removably engaged to the rear end of the adapter and extending rearward through the length of the tube holder with a rear portion extending outward from the tube holder to permit grasping and removal of the shield when the adapter is coupled to the tube holder, the shield being configured to cover the sharpened cannula when the adapter is decoupled from the tube holder.

2. The unit of claim 1 wherein the cannula forming the forward end of the adapter is a blunt cannula.

3. The unit of claim 1 wherein the cannula forming the forward end of the adapter is a luer connector.

4. A method for sampling blood comprising:

removably coupling an adapter to a forward end of a generally tubular tube holder, the tube holder configured to removably retain a blood sampling tube and defining a rear end opening configured to allow the insertion and removal of the tube;

grasping a rear end portion of a shield, the shield removably engaged to a rear end of the adapter and extending rearward through the length of the tube holder with the rear end portion extending outward from the rear end opening of the tube holder, the adapter extending through an opening at the forward end of the tube holder, the adapter having a rear end including a sharpened cannula which extends rearward within the tube holder and a cannula forming a forward end which extends forward from the tube holder, the shield extending about the sharpened cannula to protectively cover the sharpened cannula; and removing the shield from about the sharpened cannula and withdrawing the shield from within the tube holder.

5. The method of claim 4 further including the step of, after drawing blood, inserting the shield into the tube holder and replacing the shield about the cannula by engaging the shield to the adapter.

6. A blood sampling unit comprising:

an adapter having, at a proximal end, a cannula and, at a distal end, a pointed cannula;

a tube holder that can be coupled at a first end to the adapter, having an opening at a second end thereof; and means for removably covering the pointed cannula coupled to the adapter, the means for removably covering extending for a length of the tube holder with a portion thereof extending through the opening when the adapter is attached to the tube holder.

7. The blood sampling unit of claim 6 wherein the cannula is a blunt cannula.

8. The blood sampling unit of claim 6 wherein the means for removably covering is attached to the distal end of the adapter.

9. The blood sampling unit of claim 6 wherein the means for removably covering and the adapter can include threaded means for allowing it to be coupled to the adapter.

* * * * *